United States Patent
Dai

(10) Patent No.: US 7,108,973 B2
(45) Date of Patent: Sep. 19, 2006

(54) HUMAN PEN11B-RELATED GENE VARIANT ASSOCIATED WITH LUNG CANCERS

(76) Inventor: Ken-Shwo Dai, 1F., No. 18, Industry E. Rd., IV, Science-Based Industrial Park, Hsinchu (TW)

( * ) Notice: Subject to any disclaimer, the term of this patent is extended or adjusted under 35 U.S.C. 154(b) by 150 days.

(21) Appl. No.: 10/102,548

(22) Filed: Mar. 20, 2002

(65) Prior Publication Data

US 2003/0190620 A1    Oct. 9, 2003

(51) Int. Cl.
*C07H 21/02*   (2006.01)
*C12H 21/04*   (2006.01)
*C12Q 1/68*    (2006.01)

(52) U.S. Cl. .......................................... 435/6; 536/23.1
(58) Field of Classification Search ............... 536/23.1; 435/183, 325, 69.1, 7.23, 6
See application file for complete search history.

(56) References Cited

FOREIGN PATENT DOCUMENTS

WO      WO 9738131 A1 * 10/1997

OTHER PUBLICATIONS

"On the preparation and utilization of isolated and purified oligonucleotides" [electronic resource], Andrew Chin, allegedly deposited in UNC library on Mar. 14, 2002, date of publication, if any, is in question.

Sethi, T. "Science, medicine, and the future: Lung cancer" *BMJ*, 314(7081): 652, (1997).

Kondo, M., et al. "Selective maternal-allele loss in human lung cancers of the maternally expressed $p57^{KIP2}$ gene at 11p15.5" *Oncogene*, vol. 12, p. 1365-1368, (1996).

Xu, X.L, et al. "Inactivation of Human SRBC, Located within the 11p15.5-p15.4 Tumor Suppressor Region, in Breast and Lung Cancers" *Cancer Research*, vol. 61, p. 7943-7949, (2001).

* cited by examiner

*Primary Examiner*—Jeff Siew
*Assistant Examiner*—Brandon Fetterolf
(74) *Attorney, Agent, or Firm*—Ladas & Parry LLP

(57) ABSTRACT

The invention relates to a novel human PEN11B-related gene variant, and to the use of the nucleic acid of the gene variant in diagnosing diseases, in particular, lung cancer, e.g. small cell lung cancer.

1 Claim, 13 Drawing Sheets

FIG.1A

```
CACGCCCCCCGTCCAGCCCCAGCGTGTCGGAGGGGTGCCCTGGAGGGCGCGGGCTCAACTCCAT    60
CAAGAACAGCTTTCTGGCTCACCCCGCTTCCACCGCCGGAAACTGCAAGTTCCGACGCC       120
GGAGGAGATGTCCAACCTGACACCAGAGTCGTCCCCAGAGCTGGCGAAGAAGTCCTGGTT       180
         M  S  N  L  T  P  E  S  S  P  E  L  A  K  K  S  W  F   18
TGGGAACTTCATCAGCCTGGAAGAGGAGCAGATCTTCGTGGTCATCAAAGACAAACC         240
 G  N  F  I  S  L  E  E  E  Q  I  F  V  V  I  K  D  K  P           38
TCTGAGCTCCATCAAGGCTGACATCGTGCACGCCTTCCTGTCGATTCCCAGTCTCAGCCA       300
 L  S  S  I  K  A  D  I  V  H  A  F  L  S  I  P  S  L  S  H       58
CAGCGTCATCTCCCAAACGAGCTTCCGGGCCGAGTACAAGGCCACGGGGGGAGGCCAGCCGT   360
 S  V  I  S  Q  T  S  F  R  A  E  Y  K  A  T  G  G  P  A  V       78
GTTCCAGAAGCCGGTCAAGTTCCAGGTTGATATCACCTACACGGAGGGTGGGGAGGCA       420
 F  Q  K  P  V  K  F  Q  V  D  I  T  Y  T  E  G  G  E  A  Q       98
GAAGGAGAACGGCATCTACTCCGTCACCTTCACCCTGCTCTCAGGCCCCAGCCGTCGCTT     480
 K  E  N  G  I  Y  S  V  T  F  T  L  L  S  G  P  S  R  R  F      118
CAAGAGGGTGGTGGAGACCATCCAGGCCCAGCTGCTGAGCACACGACCCCCTGCCGGCC      540
 K  R  V  V  E  T  I  Q  A  Q  L  L  S  T  H  D  P  L  R  P      138
```

FIG.1B

```
CAGCACTTGTCAGACACCACTAACTGTATGGAAATGATGACGGGGCGGCTTTCCAAATGA   600
 S   T   C   Q   T   P   L   T   V   W   K   *                 149
ATTATCCCGAAAAGTTAACATGTCACCTCCACGAGGCCATCCTCTGTGACCGAAGGCAGC   660
TGCTGCGGGACCCGCCCCTCCCTGCTCCTGCTGTTGCTGCCGGGCAGTGAGGCCCAGCCC   720
AGCGCCCCGTCCACCCGGCAGCTCCTCGCCCTCAGCTCCGACCCCGGTCACCTGACCC    780
GGCCAGCTCGGGGAGCCTCCTCCAGCCCGCAGACCCGGACTCCCGTCACCTGACCC       840
CTCAGCAAGAACAGAGCTGCCTCCCCTCTCGTCCCCTCACCCGCCTCCCCCTTGCCTCATCT 900
GGGGCGGCTGTGGGCTCTGGGCTCCTGAGGTGGAAACAGAGACACCCCTGTG           960
GCACCAGAGCCTTCCCAGCAGGCCGCTGGGATCAGTGTTATTTATTGCC             1020
GTTTTAATTTATGGATTCTCCGCACCTCTGTTCAGGAAGGGCGGCCACATCCCCTG      1080
CCGTCTGCGCGTCTCAGGCAGTGGGGGGCTGGGCCCAGGCCCCTCTGAGGACAGAGC    1140
TGGTGGGGCGCTGGGGGCTGGGCTACTGTAAACTTAAAGAATTCCTGCAAGATAT      1200
TTTTATAAACTTTTTTTCTTGGTGGTTTTGTGTTTTAGTCCCTTGGTGTGGGGTGGGGCCGC 1260
TGGGCAGGGCCAGTTTTGTGTTCGCTCGTCATGGGTTCCGTCTTCTCTCTGCTCCTGTTCCTCTACACACAT 1320
CTAAAGACGGTGCGCTCGGCTGCGGTCCGTCTCTCTCTGTGGAGAAGCAGCTC        1380
CACCCTCTCGGGCTCGGGGCTGTGTCTCTCGTAGCGGGCGGCAGCGCCAGTC         1440
CCCCTCTGTCAGGCTGGGGCAATCTTGGTTTTGTGTCCAAAGGTGAAGGGTAGGAGGAG    1500
```

FIG.1C

```
GGCCCTCAGCTGGCCCCTCCCCACACACAGGACGGCAGGGGCACTGTGAGGCTTTTCTTAT    1560
TAAAATGAAAAAAATTGAAAAAAAGGACAAAGAGTCGGTGGCGCTCCTCTGCAGGGCGTT     1620
CTGTGCAGAGGCCCAGGCGAGGCCACTCAGGAGGCTCAGGCCCACCCTGCCCAGTGCCC      1680
GCCGCCGTGCTTCACCCCAGCTCTCCAGCTTCTGTGTTCCCTTCCGCCCATGTGCCCAGCCC   1740
TCCCAGGCGGGCACAGCCCGGTGCGGCCGTGGGGACGGCGGGTCTGATGCATGCC          1800
TCTGCCATGGAGTCGTCTGTCTGCTTCGGTGTCCCTGCCTCCACCCACCTCGTGT          1860
ATAGATTTTAACGCTTCTGTTAACATTAGACCTCTGCCACAGCTGGGATTCTATACAT       1920
AAGAACAAAAGCAAACACCTAGGACAGCAAACGCCCAGGCGGTACAGGCGAAGGGGCTC      1980
TCCACGGAGATCGAGGACACGAAGCAAACTGCCTCTTGCCTTCCCCTTTGTGCTTT         2040
CGGACACACGCGGACTCCAGCAGCGCCACGGAAATGGGCAAGCCCCTGCAGTGTACCCC      2100
TGTCATAACTGTGAGCAGCTGCAGCTCCGGAACAATAAATCCCTTCCGAAAGACAAAAA     2160
AAAAAAAAAAA                                                      2173
```

FIG.2A

```
         1                                                           60
PEN11BV  CACGCCCCCGTCCAGCCCCCAGCGTCGGAGGGTGCCCTGGAGGGCGGCTCAACTCCAT
PEN11B   CACGCCCCCGTCCAGCCCCCAGCGTCGGAGGGTGCCCTGGAGGGCGGCTCAACTCCAT 61                                                          120
PEN11BV  CAAGAACAGCTTTCTGGGCTCACCCCGCTTCCACCGCCGGAAACTGCAAGTTCCGACGCC
PEN11B   CAAGAACAGCTTTCTGGGCTCACCCCGCTTCCACCGCCGGAAACTGCAAGTTCCGACGCC 121                                                         180
PEN11BV  GGAGGAGATGTCCAACCTGACACCAGAGTCGTCCCCAGAGCTGGCGAAGAAGTCCTGGTT
PEN11B   GGAGGAGATGTCCAACCTGACACCAGAGTCGTCCCCAGAGCTGGCGAAGAAGTCCTGGTT 181                                                         240
PEN11BV  TGGGAACTTCATCAGCCTGGAGAAGGAGGAGCAGATCTTCGTGGTCATCAAAGACAAACC
PEN11B   TGGGAACTTCATCAGCCTGGAGAAGGAGGAGCAGATCTTCGTGGTCATCAAAGACAAACC
```

FIG.2B

```
         241                                                        300
PEN11BV  TCTGAGCTCCATCAAGGCTGACATCGTGCACGCCCTTCCTGTCGATTCCCAGTCTCAGCCA
PEN11B   TCTGAGCTCCATCAAGGCTGACATCGTGCACGCCCTTCCTGTCGATTCCCAGTCTCAGCCA 301                                                        360
PEN11BV  CAGCGGTCATCTCCCAAACGAGCTTCCGGGCCGAGTACAAGGCCACGGGGGCCAGCCGT
PEN11B   CAGCGGTCATCTCCCAAACGAGCTTCCGGGCCGAGTACAAGGCCACGGGGGCCAGCCGT 361                                                        420
PEN11BV  GTTCCAGAAGCCGGTCAAGTTCCAGGTTGATATCACCTACACGGAGGGTGGGGAGGCGCA
PEN11B   GTTCCAGAAGCCGGTCAAGTTCCAGGTTGATATCACCTACACGGAGGGTGGGGAGGCGCA 421                                                        480
PEN11BV  GAAGGAGAACGGCATCTACTCCGTCACCCTGCTCTCAGGCCCCAGCCGTCGCTT
PEN11B   GAAGGAGAACGGCATCTACTCCGTCACCCTTCACCCTGCTCTCAGGCCCCAGCCGTCGCTT
```

FIG.2C

```
        481                                                         540
PEN11BV CAAGAGGGTGGTGGAGAGACCATCCAGGCCCTGAGCTGCTGAGCACACGACCCCTGCGGCC
PEN11B  CAAGAGGGTGGTGGAGAGACCATCCAGGCCCTGAGCTGCTGAGCACACGACCCCCTGCGGCC 541                                                         600
PEN11BV CAGCACTTGTCAGACACCACTAACTGTATGGAAATGATGACGGGGCGGCTTTCCAAATGA
PEN11B  CAGCACTTGTCAGACACCACTAACTGTATGGAAATGATGACGGGGCGGCTTTCCAAATGA 601                                                         660
PEN11BV ATTATCCCGAAAAGTTAACATGTCACCTCCACGAGGCCATCCTCTGTGACCGAAGGCAGC
PEN11B  ATTATCCCGAAAAGTTAACATGTCACCTCCACGAGGCCATCCTCTGTGACCGAAGGCAGC 661                                                         720
PEN11BV TGCTGCGGACCCGCCCCTCCCGCTCCTGCTGTTGCTGCGGGCAGTGAGGCCCAGCCC
PEN11B  TGCTGCGGACCCGCCCCTCCCGCTCCTGCTGTTGCTGCGGGCAGTGAGGCCCAGCCC
```

FIG.2D

```
         721                                                            780
PEN11BV  AGCGCCCCGTCCACCCCGGGCAGCTCCTCGCCTCAGCTCCGCACGGCCCGTGGGAGGAA
PEN11B   AGCGCCCCGTCCACCCCGCGGCAGCTCCTCGCCTCAGCTCCGCACGGCCCGTGGGAGGAA 781                                                            840
PEN11BV  GGCCAGGCTCGGGGGAGCCTCCTCCAGCCCGGACCCGGACTCCCGGTCACCTGACCC
PEN11B   GGCCAGGCTCGGGGGAGCCTCCTCCAGCCCGGACCCGGACTCCCGGTCACCTGACCC 841                                                            900
PEN11BV  CTCAGCAAGAACAGC---------------------------------------------
PEN11B   CTCAGCAAGAACAGCCTGCCTGGTGGCCTTCTGGGGCCAGGACCCCGGTGGGCAACGTA 901                                                            960
PEN11BV  ------------------------------------------------------------
PEN11B   GCCACAGGAACAGGCCCCGTCCACCGCCTCCACGCCCGACCTGGAGGCCTCCTCGCAGGC
```

FIG.2E

```
         961                                                          1020
PEN11BV  ------------------------------------------------------- TGCCT
PEN11B   CCGTGCCCCGCCTCCCTGGCGGCGCCGCCTCCGTGTAGTCTTGGCCTCCTCAGGCTGCCT 1021                                                         1080
PEN11BV  CCCGTCCTCCTCTGTCTCACCCGGCCTCCCTTGCCTCCTCATCTCGGGGCGGCGTGTGGGGCTCTGG
PEN11B   CCCGTCCTCCTCTGTCTCACCCGCGCCTCCCTTGCCTCCTCATCTCGGGGGCGGCGTGTGGGGCTCTGG 1081                                                         1140
PEN11BV  CGCTCCTCCTCTGGCTGAGGTGGAAACAGAGACACCCTGTGGCACCAGAGCCTTCCCAGCA
PEN11B   CGCTCCTCCTCTGGCTGAGGTGGAAACAGAGACACCCTGTGGCACCAGAGCCTTCCCAGCA 1141                                                         1200
PEN11BV  GGCCAGGCCGCTGGGCTGGGATCAGTGTTATTTATTTGCCGTTTTAATTTATGGATTCTC
PEN11B   GGCCAGGCCGCTGGGCTGGGATCAGTGTTATTTATTTGCCGTTTTAATTTATGGATTCTC
```

FIG.2F

```
         1201                                                          1260
PEN11BV  CGCACCCTCTGTTCAGGGAAGGGCGGCGGCCACATCCCCTGCCGTCTGCGCGTCTCAGGCA
PEN11B   CGCACCCTCTGTTCAGGGAAGGGCGGCGGCCACATCCCCTGCCGTCTGCGCGTCTCAGGCA 1261                                                          1320
PEN11BV  GTGGGGGGGCTGGGGCCAGGGCGCCCCTCTGAGGACAGAGCTGGTGGGCGCGGGGGGCT
PEN11B   GTGGGGGGGCTGGGGCCAGGGCGCCCCTCTGAGGACAGAGCTGGTGGGCGCGGGGGGCT 1321                                                          1380
PEN11BV  GGCGAGCTACTGTAAACTTTAAAGAATTCCTGCAAGATATTTTATAAACTTTTTTTTCT
PEN11B   GGCGAGCTACTGTAAACTTTAAAGAATTCCTGCAAGATATTTTATAAACTTTTTTTTCT 1381                                                          1440
PEN11BV  TGGTGGTTTTTGGAAAAGGGTGTGGGGGTGGGGGCGCGCTGGGCAGGGCCAGGTTTTG
PEN11B   TGGTGGTTTTTGGAAAAGGGTGTGGGGGTGGGGGCGCGCTGGGCAGGGCCAGGTTTTG
```

FIG.2G

```
         1441                                                        1500
PEN11BV  TGTTTTAGTCCCCTGCTCCTGCTTCTTTCTACACACACATCTAAAGACGGTGCGGCTCGC
PEN11B   TGTTTTAGTCCCCTGCTCCTGCTTCTTTCTACACACACATCTAAAGACGGTGCGGCTCGC 1501                                                        1560
PEN11BV  TCTGTCATGGGTTCCGTCTCTCTCTGTGGAGAAGCAGCTCCACCTCTGGGGGGCTCGGG
PEN11B   TCTGTCATGGGTTCCGTCTCTCTCTGTGGAGAAGCAGCTCCACCTCTGGGGGGGCTCGGG 1561                                                        1620
PEN11BV  GCAGAGGGGCGGTGTCTCGTAGCGGGCGGCAGCGCCAGTCCCCCTCTGTCAGGCTGGGGC
PEN11B   GCAGAGGGGCGGTGTCTCGTAGCGGGCGGCAGCGCCAGTCCCCCTCTGTCAGGCTGGGGC 1621                                                        1680
PEN11BV  AATCTTGGTTTTGTGTCCAAAGGTGAAGGGGTAGGAGGAGGGCCCTCAGCTGGCCCTCCC
PEN11B   AATCTTGGTTTTGTGTCCAAAGGTGAAGGGGTAGGAGGAGGGCCCTCAGCTGGCCCCTCCC
```

FIG.2H

```
         1681                                                          1740
PEN11BV  CACACACAGGACGGCAGGGGCACTGTGAGGCTTTTCTTATTAAAATGAAAAAATTGAAAA
PEN11B   CACACACAGGACGGCAGGGGCACTGTGAGGCTTTTCTTATTAAAATGAAAAAATTGAAAA 1741                                                          1800
PEN11BV  AAAAGGACAAAGAGTCGGTGGCGCTCCTCTGCAGGGCGTTCTGTGCAGAGCGAGGCCCAG
PEN11B   AAAAGGACAAAGAGTCGGTGGCGCTCCTCTGCAGGGCGTTCTGTGCAGAGCGAGGCCCAG 1801                                                          1860
PEN11BV  GGCGCACTCAGGAGGGCTCAGGCCCACCCTGCCCCTGCCCCAGTGCCCCGCCCGTGCTTCACCCCAG
PEN11B   GGCGCACTCAGGAGGGCTCAGGCCCACCCTGCCCCTGCCCCAGTGCCCCGCCCGTGCTTCACCCCAG 1861                                                          1920
PEN11BV  CTCCAGCTTCTGTGTTCCCTTCCGCCCCATGTGCCCAGCCCTCCCAGGCGGGCACAGCCCG
PEN11B   CTCCAGCTTCTGTGTTCCCTTCCGCCCCATGTGCCCAGCCCTCCCAGGCGGGCACAGCCCG
```

FIG.2I

```
            1921                                                              1980
PEN11BV  GGTGCGGCGGCCGTGGGGACGGCGCGGGTCTGATGCATGCCTCTGCCATGGAGTCGTCTGT
PEN11B   GGTGCGGGCGGCCGTGGGGACGGCGCGGGTCTGATGCATGCCTCTGCCATGGAGTCGTCTGT 1981                                                              2040
PEN11BV  CTGCTTCGGTGCCTGCCCCTGCCTCCCACCCACCTCGTGTATAGATTTTAACGCTTCTGT
PEN11B   CTGCTTCGGTGCCTGCCCCTGCCTCCCACCCACCTCGTGTATAGATTTTAACGCTTCTGT 2041                                                              2100
PEN11BV  TAACATTAGACCCTCTGCCACAGGCTGGGATTTCTATACATAAGAACAAAAGCAAACACCT
PEN11B   TAACATTAGACCCTCTGCCACAGGCTGGGATTTCTATACATAAGAACAAAAGCAAACACCT 2101                                                              2160
PEN11BV  AGGACAGCAAACGCCAGGCGGTACAGGCGGGAAGGGCTCTCCACGGAGATCGAGGACAC
PEN11B   AGGACAGCAAACGCCAGGCGGTACAGGCGGGAAGGGCTCTCCACGGAGATCGAGGACAC
```

FIG.2J

```
         2161                                                    2220
PEN11BV  GAAGCAAACTGCCTCTCTTGCTTGCCTTCCCCTTTTGTGCTTCGGACACACGCGGACTCCAG
PEN11B   GAAGCAAACTGCCTCTCTTGCTTGCCTTCCCCTTTTGTGCTTCGGACACACGCGGACTCCAG 2221                                                    2280
PEN11BV  CAGGCGCCACGGAAATGGGCAAGCCCCTGCAGTGTACCCCTGTCATAACTGTGAGCAGCT
PEN11B   CAGGCGCCACGGAAATGGGCAAGCCCCTGCAGTGTACCCCTGTCATAACTGTGAGCAGCT

2281
PEN11BV  GCAGCTCCGGAACAATAAATCCCTTCCCGCAAAGACAAAAAAAAAAAAAAAAAAAA          2173
PEN11B   GCAGCTCCGGAACAATAAATCCCTTCCCGCAAAGACAAAAAAAAAAAAAAAAAAAAAAAA      2333
```

HUMAN PEN11B-RELATED GENE VARIANT ASSOCIATED WITH LUNG CANCERS

FIELD OF THE INVENTION

The invention relates to the nucleic acid of a novel human PEN11B-related gene variant, and the uses of the same in diagnosing diseases associated with the deficiency of PEN11B gene, in particular, lung cancers, e.g. small cell lung cancer (SCLC).

BACKGROUND OF THE INVENTION

Lung cancer is one of the major causers of cancer-related deaths in the world. There are two primary types of lung cancers: small cell lung cancer and non-small cell lung cancer (NSCLC) (Carney, (1992a) Curr. Opin. Oncol. 4:292–8). Small cell lung cancer accounts for approximately 25% of lung cancer and spreads aggressively (Smyth et al. (1986) Q J Med. 61: 969–76; Carney, (1992b) Lancet 339: 843–6). Non-small cell lung cancer represents the majority (about 75%) of lung cancer and is further divided into three main subtypes: squamous cell carcinoma, adenocarcinoma, and large cell carcinoma (Ihde and Minna, (1991) Cancer 15: 105–54). In recent years, much progress has been made toward understanding the molecular and cellular biology of lung cancers. Many important contributions have been made by the identification of several key genetic factors associated with lung cancers. However, the treatments of lung cancers still mainly depend on surgery, chemotherapy, and radiotherapy. This is because the molecular mechanisms underlying the pathogenesis of lung cancers remain largely unclear.

A recent hypothesis suggested that lung cancer is caused by genetic mutations of at least 10 to 20 genes (Sethi, (1997) BMJ. 314: 652–655). Therefore, future strategies for the prevention and treatment of lung cancers will be focused on the elucidation of these genetic substrates, in particular, the genes localized on chromosome 11p15.5, a region shown to be associated with the development of lung cancer (Kondo et al. (1996) Oncogene 12:1365–8; O'Briant and Bepler, (1997) Genes Chromosomes Cancer 18:111–4; Sanchez-Cespedes et al. (1997) Clin Cancer Res 3:1229–35; Bepler et al. (1998) Cancer Detect Prev 22:14–9; Pitterle et al. (1999) Mamm Genome 10:916–22; Xu et al. (2001) Cancer Res 61:7943–9). A human PEN11B gene was mapped on this region (GenBank Accession No. AF020089), suggesting that PEN11B gene may have a role in the tumorigenic process of lung cancer. Therefore, the discovery of gene variants of PEN11B may be important targets for diagnostic markers of lung cancers.

SUMMARY OF THE INVENTION

The present invention provides a PEN11B-related gene variant and the fragments thereof. The nucleotide sequence of the gene variant can be used for the diagnosis of diseases associated with the deficiency of PEN11B gene, in particular, lung cancers, e.g. SCLC.

The invention also provides methods for diagnosing diseases associated with the deficiency of PEN11B gene, in particular, lung cancers, e.g. small cell lung cancer.

BRIEF DESCRIPTION OF THE DRAWINGS

FIGS. 1A; 1B and 1C show the nucleic acid sequence (SEQ ID NO: 1) and the encoded amino acid sequence (SEQ ID NO: 2) of PEN11BV.

FIGS. 2A–2J show the nucleotide sequence alignment between the human PEN11B gene (SEQ ID NO: 5) and PEN11BV (SEQ ID NO: 1).

DETAILED DESCRIPTION OF THE INVENTION

According to the present invention, all technical and scientific terms used have the same meanings as commonly understood by persons skilled in the art.

The term "base pair (bp)" used herein denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool (BLAST; Altschul et al., (1997) Nucleic Acids Res. 25: 3389–3402)" used herein denotes programs for evaluation of homologies between a query sequence (amino or nucleic acid) and a test sequence as described by Altschul et al. (Nucleic Acids Res. 25: 3389–3402, 1997). Specific BLAST programs are described as follows:

(1) BLASTN compares a nucleotide query sequence against a nucleotide sequence database;

(2) BLASTP compares an amino acid query sequence against a protein sequence database;

(3) BLASTX compares the six-frame conceptual translation products of a query nucleotide sequence against a protein sequence database;

(4) TBLASTN compares a query protein sequence against a nucleotide sequence database translated in all six reading frames; and (5) TBLASTX compares the six-frame translations of a nucleotide query sequence against the six-frame translations of a nucleotide sequence database.

The term "cDNA" used herein denotes nucleic acids that synthesized from a mRNA template using reverse transcriptase.

The term "cDNA library" used herein denotes a library composed of complementary DNAs which are reverse-transcribed from mRNAs.

The term "complement" used herein denotes a polynucleotide sequence capable of forming base pairing with another polynucleotide sequence. For example, the sequence 5'-ATGGACTTACT-3' SEQ ID NO: 3 binds to the complementary sequence 5'-AGTAAGTCCAT-3' SEQ ID NO: 4.

The term "deletion" used herein denotes a removal of a portion of one or more amino acid residues/nucleotides from a gene.

The term "expressed sequence tags (ESTs)" used herein denotes short (200 to 500 base pairs) nucleotide sequence that derives from either 5' or 3' end of a cDNA.

The term "in silico" used herein denotes a process of using computational methods (e.g., BLAST) to analyze DNA sequences.

The term "polymerase chain reaction (PCR)" used herein denotes a method which increases the copy number of a nucleic acid sequence using a DNA polymerase and a set of primers (about 20 bp oligonucleotides complementary to each strand of DNA) under suitable conditions (successive rounds of primer annealing, strand elongation, and dissociation).

The term "nucleic acid sequence" or "polynucleotide" used herein denotes a sequence of nucleotide (guanine, cytosine, thymine or adenine) in a specific order that can be a natural or synthesized fragment of DNA or RNA. It may be single-stranded or double-stranded.

The term "reverse transcriptase-polymerase chain reaction (RT-PCR)" used herein denotes a process which transcribes mRNA to complementary DNA strand using reverse transcriptase followed by polymerase chain reaction to amplify the specific fragment of DNA sequences.

The term "transformation" used herein denotes a process describing the uptake, incorporation, and expression of exogenous DNA by prokaryotic host cells.

The term "transfection" used herein a process describing the uptake, incorporation, and expression of exogenous DNA by eukaryotic host cells.

The term "variant" used herein denotes a fragment of sequence (nucleotide or amino acid) inserted or deleted by one or more nucleotides/amino acids.

The present invention in the first aspect provides a novel human PEN11B-related gene variant and the fragments thereof.

According to the present invention, human PEN11B cDNA sequence was used to query the human lung EST databases (a normal lung, a large cell lung cancer, a squamous cell lung cancer and a small cell lung cancer) using BLAST program to search for PEN11B-related gene variants. One human cDNA partial sequence (i.e., EST) showing similarity to PEN11B was identified from the ESTs deposited in the SCLC database. The cDNA clone, named PEN11BV (PEN11B variant), was then isolated from the SCLC cDNA library and sequenced. FIGS. 1A–1C show the nucleic acid sequence (SEQ ID NO:1) and the encoded amino acid sequence of PEN11BV.

The full-length of the PEN11BV cDNA is a 2173 bp clone containing a 447 bp open reading frame (ORF) extending from 128 bp to 574 bp, which corresponds to an encoded protein of 149 amino acid residues with a predicted molecular mass of 16.6 kDa. The sequence around the initiation ATG codon of PEN11BV (located at nucleotide 128 to 130 bp) was similar to the Kozak consensus sequence (A/GC-CATGG) (Kozak, (1987) Nucleic Acids Res. 15: 8125–48; Kozak, (1991) J Cell Biol. 115: 887–903.).

To determine the variation in sequence of PEN11BV cDNA clone, an alignment of PEN11B nucleotide sequence with PEN11BV was performed (FIGS. 1A–2J). One major genetic deletion was found in the aligned sequences, showing that PEN11BV is a 160 bp deletion in the sequence of PEN11B from 856–1015 bp. This deletion occurs on the 3'-untranslated region (3'UTR). Thus, no change can be observed on the predicted amino acid sequence of PEN11BV as compared with that of PEN11B.

In the present invention, a search of ESTs deposited in dbEST (Boguski et al. (1993) Nat Genet. 4: 332–3) at National Center of Biotechnology Information (NCBI) was performed to determine the tissue distribution of PEN11BV in silico. The result of in silico Northern analysis showed that one EST (GenBank Accession Number BE264379) was found to confirm the absence of 160 bp region on PEN11BV nucleotide sequence. This EST was generated from a SCLC cDNA library, suggesting that the absence of 160 bp nucleotide fragment located between nucleotides 855 to 856 of PEN11BV may serve as a useful marker for diagnosing diseases associated with the deficiency of PEN11B gene, in particular, lung cancers, e.g. SCLC. Therefore, any nucleotide fragments comprising nucleotides 855 to 856 of PEN11BV may be used as probes for determining the presence of PEN11BV under highly stringent conditions. An alternative approach is that any set of primers for amplifying the fragment containing nucleotides 855 to 856 of PEN11BV may be used for determining the presence of the variant.

According to the present invention, the fragments of the nucleic acid sequences of the human PEN11BV can be used as primers or probes. Preferably, the purified fragments of the human PEN11BV are used. The fragments may be produced by enzymatic digestion, chemical cleavage of isolated or purified nucleic acid sequences, or chemical synthesis and then may be isolated or purified. Such isolated or purified fragments of the nucleic acid sequences can be directly used as primers or probes.

Many gene variants have been found to be associated with diseases (Stallings-Mann et al., (1996) Proc Natl Acad Sci U S A 93: 12394–9; Liu et al., (1997) Nat Genet 16:328–9; Siffert et al., (1998) Nat Genet 18: 45 to 8; Lukas et al., (2001) Cancer Res 61: 3212 to 9). Since PEN11BV clone was isolated from SCLC cDNA library and its expression in SCLC was confirmed by in silico Northern analysis, it is advisable that PEN11BV may serve as a marker for the diagnosis of diseases associated with the deficiency of PEN11B gene, in particular, lung cancers, e.g. SCLC. Thus, the expression level of PEN11BV relative to PEN11B may be a useful indicator for screening of patients suspected of having such diseases, and the index of relative expression level (mRNA) may confer an increased susceptibility to such diseases.

Accordingly, the subject invention in a further aspect provides methods for diagnosing diseases associated with the deficiency of PEN11B gene in a mammal, in particular, lung cancers, e.g. small cell lung cancer.

The method for diagnosing the diseases associated with the deficiency of PEN11B gene may be performed by detecting the nucleotide sequence of the human PEN11BV of the invention which comprises the steps of: (1) extracting total RNA of cells obtained from a mammal; (2) amplifying the RNA by reverse transcriptase-polymerase chain reaction (RT-PCR) with a set of primers to obtain a cDNA comprising the fragments comprising nucleotides 853 to 858 of SEQ ID NO: 1; and (3) detecting whether the cDNA sample is obtained. If necessary, the amount of the obtained cDNA sample may be detected.

In the above embodiment, one of the primers may be designed to have a sequence comprising the nucleotides of SEQ ID NO: 1 containing nucleotides 853 to 858, and the other may be designed to have a sequence complementary to the nucleotides of SEQ ID NO: 1 at any other locations downstream of nucleotide 858. Alternatively, one of the primers may be designed to have a sequence complementary to the nucleotides of SEQ ID NO: 1 containing nucleotides 853 to 858, and the other may be designed to have a sequence comprising the nucleotides of SEQ ID NO: 1 at any other locations upstream of nucleotide 853. In this case, only PEN11BV will be amplified.

Alternatively, one of the primers may be designed to have a sequence comprising the nucleotides of SEQ ID NO: 1 upstream of nucleotide 855 and the other may be designed to have a sequence complementary to the nucleotides of SEQ ID NO: 1 downstream of nucleotide 856. Alternatively, one of the primers may be designed to have a sequence complementary to the nucleotides of SEQ ID NO: 1 upstream of nucleotide 855 and the other may be designed to have a sequence comprising the nucleotides of SEQ ID NO: 1 downstream of nucleotide 856. In this case, both PEN11B and PEN11BV will be amplified. The length of the PCR fragment from PEN11BV will be 160 bp shorter than that from PEN11B.

Preferably, the primer of the invention contains 15 to 30 nucleotides.

Total RNA may be isolated from patient samples by using TRIZOL reagents (Life Technology). Tissue samples (e.g., biopsy samples) are powdered under liquid nitrogen before homogenization. RNA purity and integrity are assessed by absorbance at 260/280 nm and by agarose gel electrophoresis. The set of primers designed to amplify the expected size of specific PCR fragments of PEN11BV can be used. PCR fragments are analyzed on a 1% agarose gel using five microliters (10%) of the amplified products. To determine the expression level of the gene variant, the intensity of the PCR products may be determined by using the Molecular Analyst program (version 1.4.1; Bio-Rad).

The RT-PCR experiment may be performed according to the manufacturer's instructions (Boehringer Mannheim). A 50 µl reaction mixture containing 2 µl total RNA (0.1 µg/µl), 1 µl each primer (20 pM), 1 µl each dNTP (10 mM), 2.5 µl DTT solution (100 mM), 10 µl 5× RT-PCR buffer, 1 µl enzyme mixture, and 28.5 µl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

Another embodiment for diagnosing the diseases associated with the deficiency of PEN11B gene may be performed by detecting the nucleotide sequences of the human PEN11BV of the invention which comprises the steps of: (1) extracting total RNA from a sample obtained from the mammal; (2) amplifying the RNA by reverse transcriptase-polymerase chain reaction (RT-PCR) to obtain a cDNA sample; (3) bringing the cDNA sample into contact with the nucleic acid of SEQ ID NO: 1 and the fragments thereof; and (4) detecting whether the cDNA sample hybridizes with the nucleic acid of SEQ ID NO: 1 or the fragments thereof. If necessary, the amount of hybridized sample may be detected.

The expression of gene variants can be analyzed using Northern Blot hybridization approach. Specific fragment comprising nucleotides 853 to 858 of the PEN11BV may be amplified by polymerase chain reaction (PCR) using primer set designed for RT-PCR. The amplified PCR fragment may be labeled and serve as a probe to hybridize the membranes containing total RNAs extracted from the samples under the conditions of 55° C. in a suitable hybridization solution for 3 hr. Blots may be washed twice in 2×SSC, 0.1% SDS at room temperature for 15 minutes each, followed by two washes in 0.1×SSC and 0.1% SDS at 65° C. for 20 minutes each. After these washes, blot may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of gene variants (cDNAs or PCR) can be detected using microarray (bio-chip) approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray (bio-chip), can be determined by analyzing the scanned images.

The following examples are provided for illustration, but not for limiting the invention.

EXAMPLES

Analysis of Human Lung EST Databases

Expressed sequence tags (ESTs) generated from the large-scale PCR-based sequencing of the 5'-end of human lung (normal, SCLC, squamous cell lung cancer and large cell lung cancer) cDNA clones were compiled and served as EST databases. Sequence comparisons against the nonredundant nucleotide and protein databases were performed using BLASTN and BLASTX programs (Altschul et al., (1997) Nucleic Acids Res. 25:3389–3402; Gish and States, (1993) Nat Genet 3:266–272), at the National Center for Biotechnology Information (NCBI) with a significance cutoff of $p<10^{-10}$. ESTs representing putative PEN11BV gene were identified during the course of EST generation.

Isolation of cDNA Clones

One cDNA clone exhibiting EST sequence similar to the PEN11B gene was isolated from the SCLC cDNA library and named PEN11BV. The inserts of these clones were subsequently excised in vivo from the λZAP Express vector using the ExAssist/XLOLR helper phage system (Stratagene). Phagemid particles were excised by coinfecting XL 1-BLUE MRF' cells with ExAssist helper phage. The excised pBluescript phagemids were used to infect *E. coli* XLOLR cells, which lack the amber suppressor necessary for ExAssist phage replication. Infected XLOLR cells were selected using kanamycin resistance. Resultant colonies contained the double stranded phagemid vector with the cloned cDNA insert. A single colony was grown overnight in LB-kanamycin, and DNA was purified using a Qiagen plasmid purification kit.

Full Length Nucleotide Sequencing and Database Comparisons

Phagemid DNA was sequenced using the Epicentre#SE9101LC SequiTherm EXCEL™II DNA Sequencing Kit for 4200S-2 Global NEW IR² DNA sequencing system (LI-COR). Using the primer-walking approach, full-length sequence was determined. Nucleotide and protein searches were performed using BLAST against the non-redundant database of NCBI.

In Silico Tissue Distribution (Northern) Analysis

The coding sequence for each cDNA clones was searched against the dbEST sequence database (Boguski et al., (1993) Nat Genet. 4: 332–3) using the BLAST algorithm at the NCBI website. ESTs derived from each tissue were used as a source of information for transcript tissue expression analysis. Tissue distribution for each isolated cDNA clone was determined by ESTs matching to that particular sequence variants (insertions or deletions) with a significance cutoff of $p<10^{-10}$.

REFERENCES

Altschul et al., Gapped BLAST and PSI-BLAST: a new generation of protein database search programs, Nucleic Acids Res, 25: 3389–3402, (1997).

Bepler et al. Association of chromosome 11 locus D11S12 with histology, stage, and metastases in lung cancer. Cancer Detect Prev, 22:14–9, (1998).

Boguski et al., dbEST—database for "expressed sequence tags". Nat Genet. 4: 332–3, (1993).

Carney, D. N. The biology of lung cancer. Curr. Opin. Oncol. 4: 292–8, (1992a).

Carney, D. N. Biology of small-cell lung cancer. Lancet 339: 843–6, (1992b).

Gish and States, Identification of protein coding regions by database similarity search, Nat Genet, 3:266–272, (1993).

Ihde and Minna, Non-small cell lung cancer. Part II: Treatment. Curr. Probl. Cancer 15: 105–54, (1991).

Kondo et al. Selective maternal-allele loss in human lung cancers of the maternally expressed p57KIP2 gene at 11p15.5. Oncogene 12:1365–8, (1996).

Kozak, An analysis of 5'-noncoding sequences from 699 vertebrate messenger RNAs. Nucleic Acids Res, 15: 8125–48, (1987).

Kozak, An analysis of vertebrate mRNA sequences: intimations of translational control, J Cell Biol, 115: 887–903, (1991).

Liu et al., Silent mutation induces exon skipping of fibrillin-1 gene in Marfan syndrome. Nat Genet 16:328–9, (1997).

Lukas et al., Alternative and aberrant messenger RNA splicing of the mdm2 oncogene in invasive breast cancer. Cancer Res 61:3212–9, (2001).

Miura and Jinno, GenBank Accession No. AF020089

O'Briant and Bepler, Delineation of the centromeric and telomeric chromosome segment 11p15.5 lung cancer suppressor regions LOH11A and LOH11B. Genes Chromosomes Cancer, 18:111–4, (1997).

Pitterle et al. Lung cancer and the human gene for ribonucleotide reductase subunit M1 (RRM1). Mamm Genome 10:916–22, (1999).

Sanchez-Cespedes et al. Microsatellite alterations at 5q21, 11p13, and 11p15.5 do not predict survival in non-small cell lung cancer. Clin Cancer Res 3:1229–35, (1997).

Sethi, Science, medicine, and the future. Lung cancer, BMJ, 314: 652–655, (1997)

Siffert et al., Association of a human G-protein beta3 subunit variant with hypertension. Nat Genet, 18:45–8, (1998).

Smyth et al., The impact of chemotherapy on small cell carcinoma of the bronchus. Q J Med, 61: 969–76, (1986).

Stallings-Mann et al., Alternative splicing of exon 3 of the human growth hormone receptor is the result of an unusual genetic polymorphism. Proc Natl Acad Sci U S A 93:12394–9, (1996).

Strausberg, R. EST Accession No. BE264379

Xu et al. Inactivation of human SRBC, located within the 11p15.5-p15.4 tumor suppressor region, in breast and lung cancers. Cancer Res, 61:7943–9, (2001).

What is claimed is:

1. An isolated nucleic acid consisting of the nucleotide sequence of SEQ ID NO: 1.

\* \* \* \* \*

```
                            SEQUENCE LISTING

<160> NUMBER OF SEQ ID NOS: 2

<210> SEQ ID NO 1
<211> LENGTH: 2173
<212> TYPE: DNA
<213> ORGANISM: Homo sapiens
<220> FEATURE:
<221> NAME/KEY: CDS
<222> LOCATION: (128)..(574)
<223> OTHER INFORMATION:

<400> SEQUENCE: 1 cacgccccg  tccagcccca  gcgtcggagg  ggtgccctgg  agggcgcggc  tcaactccat      60
caagaacagc  tttctgggct  cacccccgctt  ccaccgccgg  aaactgcaag  ttccgacgcc    120 ggaggag atg tcc aac ctg aca cca gag tcg tcc cca gag ctg gcg aag            169
        Met Ser Asn Leu Thr Pro Glu Ser Ser Pro Glu Leu Ala Lys
         1               5                  10 aag tcc tgg ttt ggg aac ttc atc agc ctg gag aag gag gag cag atc            217
Lys Ser Trp Phe Gly Asn Phe Ile Ser Leu Glu Lys Glu Glu Gln Ile
 15              20                  25                  30 ttc gtg gtc atc aaa gac aaa cct ctg agc tcc atc aag gct gac atc            265
Phe Val Val Ile Lys Asp Lys Pro Leu Ser Ser Ile Lys Ala Asp Ile
                 35                  40                  45 gtg cac gcc ttc ctg tcg att ccc agt ctc agc cac agc gtc atc tcc            313
Val His Ala Phe Leu Ser Ile Pro Ser Leu Ser His Ser Val Ile Ser
             50                  55                  60 caa acg agc ttc cgg gcc gag tac aag gcc acg ggg ggg cca gcc gtg            361
Gln Thr Ser Phe Arg Ala Glu Tyr Lys Ala Thr Gly Gly Pro Ala Val
         65                  70                  75 ttc cag aag ccg gtc aag ttc cag gtt gat atc acc tac acg gag ggt            409
Phe Gln Lys Pro Val Lys Phe Gln Val Asp Ile Thr Tyr Thr Glu Gly
     80                  85                  90
```

```
ggg gag gcg cag aag gag aac ggc atc tac tcc gtc acc ttc acc ctg      457
Gly Glu Ala Gln Lys Glu Asn Gly Ile Tyr Ser Val Thr Phe Thr Leu
 95                 100                 105                 110 ctc tca ggc ccc agc cgt cgc ttc aag agg gtg gtg gag acc atc cag      505
Leu Ser Gly Pro Ser Arg Arg Phe Lys Arg Val Val Glu Thr Ile Gln
                115                 120                 125 gcc cag ctg ctg agc aca cac gac ccc ctg cgg ccc agc act tgt cag      553
Ala Gln Leu Leu Ser Thr His Asp Pro Leu Arg Pro Ser Thr Cys Gln
            130                 135                 140 aca cca cta act gta tgg aaa tgatgacggg cggctttcc aaatgaatta          604
Thr Pro Leu Thr Val Trp Lys
                145 tcccgaaaag ttaacatgtc acctccacga ggccatcctc tgtgaccgaa ggcagctgct    664
gcggacccgc cctccctccg ctcctgctgt tgctgccggg cagtgaggcc cagcccagcg    724
ccccgtccac cccgcggcag ctcctcgcct cagctccgca cggcccgtgg gaggaaggcc    784
aggctcgggg gagcctcctc cagcccggcc gacccggact cccggtcacc tgaccctca     844
gcaagaacag ctgcctcccg tcctctcgtc tcacccgcgc ctcccttgcc tcatctgggg    904
cggctgtggg ctctggcgct cctctctggc tgaggtggaa acagagacac cctgtggcac    964
cagagccttc ccagcaggcc aggccgctgg gctgggatca gtgttattta tttgccgttt   1024
taatttatgg attctccgca cctctgttca gggaagggcg gcggccacat cccctgccgt   1084
ctgcgcgtct caggcagtgg gggggctggg gccaggcgc cctctgagga cagagctggt    1144
ggggcgcggg ggggctggcg agctactgta aactttaaag aattcctgca agatattttt   1204
ataaactttt ttttcttggt ggttttgga aaagggtgtg ggggtggggg cgccgctggg    1264
gcagggccag gttttgtgtt ttagtcccct gctcctgctt ctttctacac acacatctaa   1324
agacggtgcg gctcgctctg tcatgggttc cgtctctctc tgtggagaag cagctccacc   1384
tctgggggg ctcggggcag aggggcggtg tctcgtagcg gcggcagcg ccagtccccc     1444
tctgtcaggc tgggcaatc ttggttttgt gtccaaaggt gaagggtag gaggagggcc     1504
ctcagctggc cctccccaca cacaggacgg caggggcact gtgaggcttt tcttattaaa   1564
atgaaaaaat tgaaaaaaaa ggacaaagag tcggtggcgc tcctctgcag ggcgttctgt   1624
gcagagcgag gcccagggcg cactcaggag ggctcaggcc accctgccca gtgcccgccg   1684
ccgtgcttca ccccagctcc agcttctgtg ttcccttccg cccatgtgcc cagccctccc   1744
aggcgggcac agcccgggtg cggcggccgt ggggacggc gggtctgatg catgcctctg    1804
ccatggagtc gtctgtctgc ttcggtgcct gcccctgcct cccacccacc tcgtgtatag   1864
atttaacgc ttctgttaac attagacctc tgccacaggc tgggatttct atacataaga   1924
acaaaagcaa acacctagga cagcaaacgc caggcggtac aggcgggaag gggctctcca   1984
cggagatcga ggacacgaag caaactgcct cttgcttgcc ttccccttt gtgcttcgga    2044
cacacgcgga ctccagcagg cgccacggaa atgggcaagc ccctgcagtg taccctgtc    2104
ataactgtga gcagctgcag ctccggaaca ataaatccct tccgcaaaga caaaaaaaa    2164
aaaaaaaa                                                            2173
```

<210> SEQ ID NO 2
<211> LENGTH: 149
<212> TYPE: PRT
<213> ORGANISM: Homo sapiens

<400> SEQUENCE: 2

-continued

```
Met Ser Asn Leu Thr Pro Glu Ser Ser Pro Glu Leu Ala Lys Lys Ser
1               5                   10                  15

Trp Phe Gly Asn Phe Ile Ser Leu Glu Lys Glu Glu Gln Ile Phe Val
            20                  25                  30

Val Ile Lys Asp Lys Pro Leu Ser Ser Ile Lys Ala Asp Ile Val His
            35                  40                  45

Ala Phe Leu Ser Ile Pro Ser Leu Ser His Ser Val Ile Ser Gln Thr
            50                  55                  60

Ser Phe Arg Ala Glu Tyr Lys Ala Thr Gly Gly Pro Ala Val Phe Gln
65                  70                  75                  80

Lys Pro Val Lys Phe Gln Val Asp Ile Thr Tyr Thr Glu Gly Gly Glu
            85                  90                  95

Ala Gln Lys Glu Asn Gly Ile Tyr Ser Val Thr Phe Thr Leu Leu Ser
            100                 105                 110

Gly Pro Ser Arg Arg Phe Lys Arg Val Val Glu Thr Ile Gln Ala Gln
            115                 120                 125

Leu Leu Ser Thr His Asp Pro Leu Arg Pro Ser Thr Cys Gln Thr Pro
    130                 135                 140

Leu Thr Val Trp Lys
145
```